United States Patent
Kim et al.

(10) Patent No.: US 12,403,208 B2
(45) Date of Patent: Sep. 2, 2025

(54) METHOD AND DEVICE WITH OBJECT INACTIVATION

(71) Applicant: Samsung Electronics Co., Ltd., Suwon-si (KR)

(72) Inventors: Jongsok Kim, Hwaseong-si (KR); Jinyong Jeon, Yongin-si (KR); Ginam Kim, Seongnam-si (KR); Mimsung Eo, Anyang-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 961 days.

(21) Appl. No.: 17/363,596

(22) Filed: Jun. 30, 2021

(65) Prior Publication Data
US 2021/0402028 A1  Dec. 30, 2021

(30) Foreign Application Priority Data

Jun. 30, 2020 (KR) .................. 10-2020-0080525
Mar. 17, 2021 (KR) .................. 10-2021-0034871

(51) Int. Cl.
*A61L 2/12* (2006.01)
*A61L 2/00* (2006.01)
(Continued)

(52) U.S. Cl.
CPC .............. *A61L 2/12* (2013.01); *A61L 2/0064* (2013.01); *A61L 2/24* (2013.01); *H01Q 9/0407* (2013.01);
(Continued)

(58) Field of Classification Search
CPC . A61L 2/12; A61L 2/0064; A61L 2/24; A61L 2202/14; A61L 2202/16;
(Continued)

(56) References Cited

U.S. PATENT DOCUMENTS 7,696,930 B2   4/2010  Akkermans et al.
10,279,190 B2* 5/2019  Botsford ............ A61N 2/02
(Continued)

FOREIGN PATENT DOCUMENTS

JP       5308512 B2      10/2013
KR   10-2013-0075813 A    7/2013
(Continued)

OTHER PUBLICATIONS

Dykeman, Eric et al. "Low Frequency Mechanical Modes of Viral Capsids: An Atomistic Approach" *Arizona University Physical Review Letters PRL 100*, 028101 Jan. 14, 2008 pp. 028101-1-028101-4.
(Continued)

*Primary Examiner* — Sean E Conley
*Assistant Examiner* — Brendan A Hensel
(74) *Attorney, Agent, or Firm* — NSIP Law

(57) ABSTRACT

A device for inactivating an object, includes an electromagnetic wave generator configured to generate an electromagnetic wave having a resonant frequency of the object, and an antenna unit electrically connected to the electromagnetic wave generator and configured to omni-directionally transmit the electromagnetic wave to inactivate the object.

18 Claims, 12 Drawing Sheets

(51) Int. Cl.
*A61L 2/24* (2006.01)
*H01Q 9/04* (2006.01)
*H03B 5/36* (2006.01)

(52) U.S. Cl.
CPC ............ *H03B 5/36* (2013.01); *A61L 2202/14* (2013.01); *A61L 2202/16* (2013.01)

(58) Field of Classification Search
CPC .... H01Q 9/0407; H01Q 1/2275; H01Q 5/307; H01Q 21/24; H01Q 1/2283; H03B 5/36
See application file for complete search history.

(56) References Cited

U.S. PATENT DOCUMENTS

| | | | |
|---|---|---|---|
| 12,095,144 B1* | 9/2024 | Ichitsubo | .................. H03F 1/56 |
| 2009/0216161 A1 | 8/2009 | Brooks et al. | |
| 2024/0097739 A1* | 3/2024 | Leabman | ................ H02J 50/80 |

FOREIGN PATENT DOCUMENTS

| KR | 10-1757196 B1 | 7/2017 |
|---|---|---|
| KR | 10-2018-0114297 A | 10/2018 |

OTHER PUBLICATIONS

Yang, Szu-Chi et al. "Efficient Structure Resonance Energy Transfer from Microwaves to Confined Acoustic Vibrations in Viruses" *Scientific Reports 5:18030* Dec. 9, 2015 pp. 1-10.

* cited by examiner

FIG. 4

| ELECTRONIC DEVICES | ELECTRIC FIELD STRENGTH [V/m] |
|---|---|
| MICROWAVE OVEN @ 50 cm | 25 |
| HUMIDIFIER @ 50 cm | 30 |
| WASHING MACHINE @ 30 cm | 70 |
| HAIR DRYER @ 10 cm | 105 |
| VACUUM CLEANER @ 10 cm | 175 |

METHOD AND DEVICE WITH OBJECT INACTIVATION

CROSS-REFERENCE TO RELATED APPLICATIONS

This application claims the benefit under 35 U.S.C. § 119 of Korean Patent Application No. 10-2020-0080525, filed on Jun. 30, 2020, in the Korean Intellectual Property Office, and Korean Patent Application No. 10-2021-0034871, filed on Mar. 17, 2021, in the Korean Intellectual Property Office, the entire disclosures of which are incorporated by reference herein by reference for all purposes.

BACKGROUND

1. Field

The present disclosure relates to method and device with object inactivation.

2. Description of the Related Art

There are many known microorganisms such as cancer cells, influenza viruses, and corona viruses which are harmful to the human body.

For example, an oligodynamic action is applied in a method of disturbing the metabolism of viruses and damaging even the DNA of viruses by using metal ions (for example, copper ions). In addition, methods such as a method of destroying the DNA of microorganisms by ultraviolet irradiation, a method of inactivating microorganisms by heating them to a specific temperature range, and a method of inactivating microorganisms by using a substance having strong sterilizing power such as sodium hypochlorite or the like have been known.

However, in the method of inactivating viruses using metal ions, high costs may be incurred to obtain metal ions, and also, the metal ions may easily be oxidized. In addition, when a subject having microorganisms is irradiated with ultraviolet rays and heated, not only the microorganisms to be inactivated but also cells of the subject may be destroyed. Therefore, there is a need to develop a device and method for selectively inactivating or removing an object to be inactivated.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a device for inactivating an object, includes an electromagnetic wave generator configured to generate an electromagnetic wave having a resonant frequency of the object, and an antenna unit electrically connected to the electromagnetic wave generator and configured to omni-directionally transmit the electromagnetic wave to inactivate the object.

The object may include any one or any combination of any two or more of cells, germs, and viruses.

The electromagnetic wave generator may be further configured to generate the electromagnetic wave in a frequency band including the resonant frequency having a width of about 50% of the resonant frequency.

The electromagnetic wave generator may be further configured to generate the electromagnetic wave having a frequency within a range of about 5 GHz to about 10 GHz.

The electromagnetic wave generator may be further configured to generate the electromagnetic wave with an intensity of less than about 200 V/m.

The antenna unit may be further configured to uniformly transmit the electromagnetic wave in all directions.

The electromagnetic wave generator may include a radio frequency integrated circuit (RFIC).

The electromagnetic wave generator may further include a crystal oscillator.

The antenna unit may include a low temperature co-fired ceramic (LTCC) substrate and a patch antenna provided on an upper portion of the LTCC substrate.

The device may further include a substrate comprising a first surface and a second surface facing each other. The electromagnetic wave generator may be provided on the first surface of the substrate, and the antenna unit may be provided on the second surface of the substrate.

The electromagnetic wave generator may include a first electromagnetic wave generator configured to generate a first electromagnetic wave having a first frequency, and a second electromagnetic wave generator configured to generate a second electromagnetic wave having a second frequency different from the first frequency.

The electromagnetic wave generator may further include a third electromagnetic wave generator configured to generate a third electromagnetic wave having a third frequency different from the first frequency and the second frequency. The first frequency, the second frequency, and the third frequency may be different from each other by a constant increment size.

The device may further include a controller configured to selectively operate the first electromagnetic wave generator and the second electromagnetic wave generator.

The antenna unit may include a first antenna unit electrically connected to the first electromagnetic wave generator, and a second antenna unit electrically connected to the second electromagnetic wave generator.

An electronic device may include the device, and a mount on which the device may be mounted.

The electronic device may include at least one selected from the group consisting of a smartphone, a tablet PC, and a wearable device.

In another general aspect, a method of inactivating an object, includes generating an electromagnetic wave having a resonant frequency of the object, and transmitting the electromagnetic wave uniformly in all directions from a position adjacent to the object.

In the generating of the electromagnetic wave, the electromagnetic wave may have an intensity lower than about 200 V/m in a frequency band including the resonant frequency and a width of about 50% of the resonant frequency.

In the generating of the electromagnetic wave, the electromagnetic wave may have a frequency within a range of about 5 GHz to about 10 GHz generated.

The electromagnetic wave may be a first electromagnetic wave, and after generating and transmitting the first electromagnetic wave, the method may further include generating a second electromagnetic wave having a second frequency different from the first frequency, and transmitting the second electromagnetic wave uniformly in all directions from a position adjacent to the object.

In another general aspect, a device for inactivating microorganisms, includes an electromagnetic wave generator configured to generate electromagnetic wave having different resonant frequencies for different ones of microorganisms, and an antenna unit, connected to the electromagnetic wave generator, configured to transmit one of the electromagnetic waves to inactivate a corresponding one of the microorganisms.

The microorganisms may include cells, germs, and viruses.

Other features and aspects will be apparent from the following detailed description, the drawings, and the claims.

BRIEF DESCRIPTION OF THE DRAWINGS

FIG. 4 is a table illustrating the strength of electromagnetic waves generated from various electronic devices.

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

Figure 1:
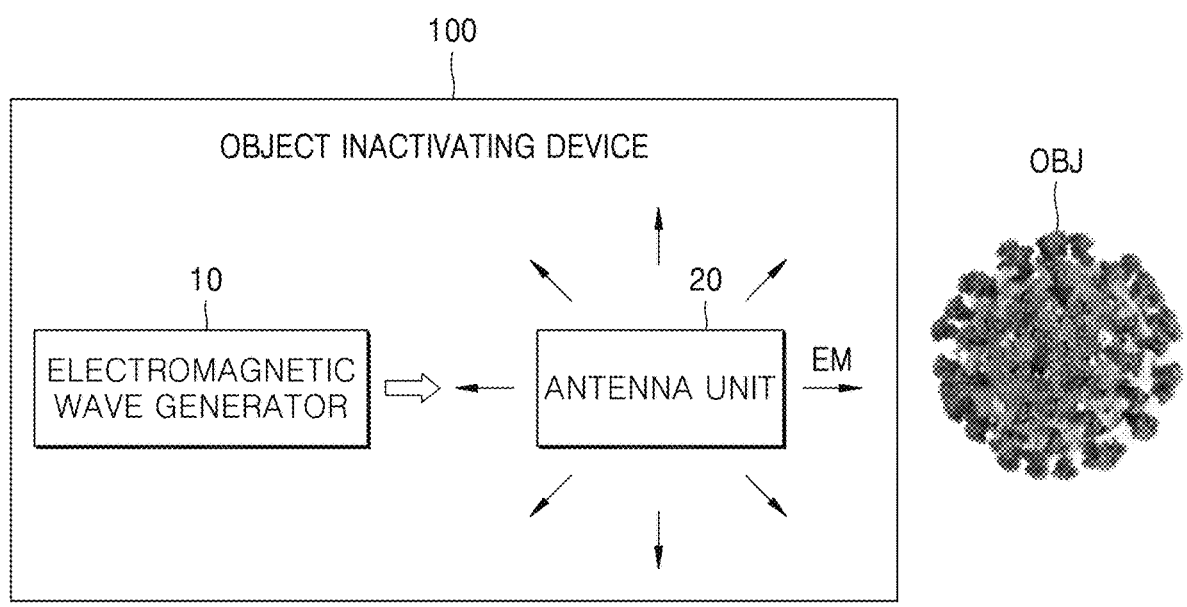
FIG. 1 is a schematic view illustrating an example structure of an object inactivating device according to an embodiment.

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known after understanding of the disclosure of this application may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

Throughout the specification, when an element, such as a layer, region, or substrate, is described as being "on," "connected to," or "coupled to" another element, it may be directly "on," "connected to," or "coupled to" the other element, or there may be one or more other elements intervening therebetween. In contrast, when an element is described as being "directly on," "directly connected to," or "directly coupled to" another element, there can be no other elements intervening therebetween.

As used herein, the term "and/or" includes any one and any combination of any two or more of the associated listed items.

Although terms such as "first," "second," and "third" may be used herein to describe various members, components, regions, layers, or sections, these members, components, regions, layers, or sections are not to be limited by these terms. Rather, these terms are only used to distinguish one member, component, region, layer, or section from another member, component, region, layer, or section. Thus, a first member, component, region, layer, or section referred to in examples described herein may also be referred to as a second member, component, region, layer, or section without departing from the teachings of the examples.

Spatially relative terms such as "above," "upper," "below," and "lower" may be used herein for ease of description to describe one element's relationship to another element as shown in the figures. Such spatially relative terms are intended to encompass different orientations of the device in use or operation in addition to the orientation depicted in the figures. For example, if the device in the figures is turned over, an element described as being "above" or "upper" relative to another element will then be "below" or "lower" relative to the other element. Thus, the term "above" encompasses both the above and below orientations depending on the spatial orientation of the device. The device may also be oriented in other ways (for example, rotated 90 degrees or at other orientations), and the spatially relative terms used herein are to be interpreted accordingly.

The terminology used herein is for describing various examples only, and is not to be used to limit the disclosure. The articles "a," "an," and "the" are intended to include the plural forms as well, unless the context clearly indicates otherwise. The terms "comprises," "includes," and "has" specify the presence of stated features, numbers, operations, members, elements, and/or combinations thereof, but do not preclude the presence or addition of one or more other features, numbers, operations, members, elements, and/or combinations thereof.

Due to manufacturing techniques and/or tolerances, variations of the shapes shown in the drawings may occur. Thus, the examples described herein are not limited to the specific shapes shown in the drawings, but include changes in shape that occur during manufacturing.

The features of the examples described herein may be combined in various ways as will be apparent after an understanding of the disclosure of this application. Further, although the examples described herein have a variety of configurations, other configurations are possible as will be apparent after an understanding of the disclosure of this application.

The present disclosure relates to a device and method for inactivating an object by using an electromagnetic wave having a resonant frequency of the object.

Figure 2:
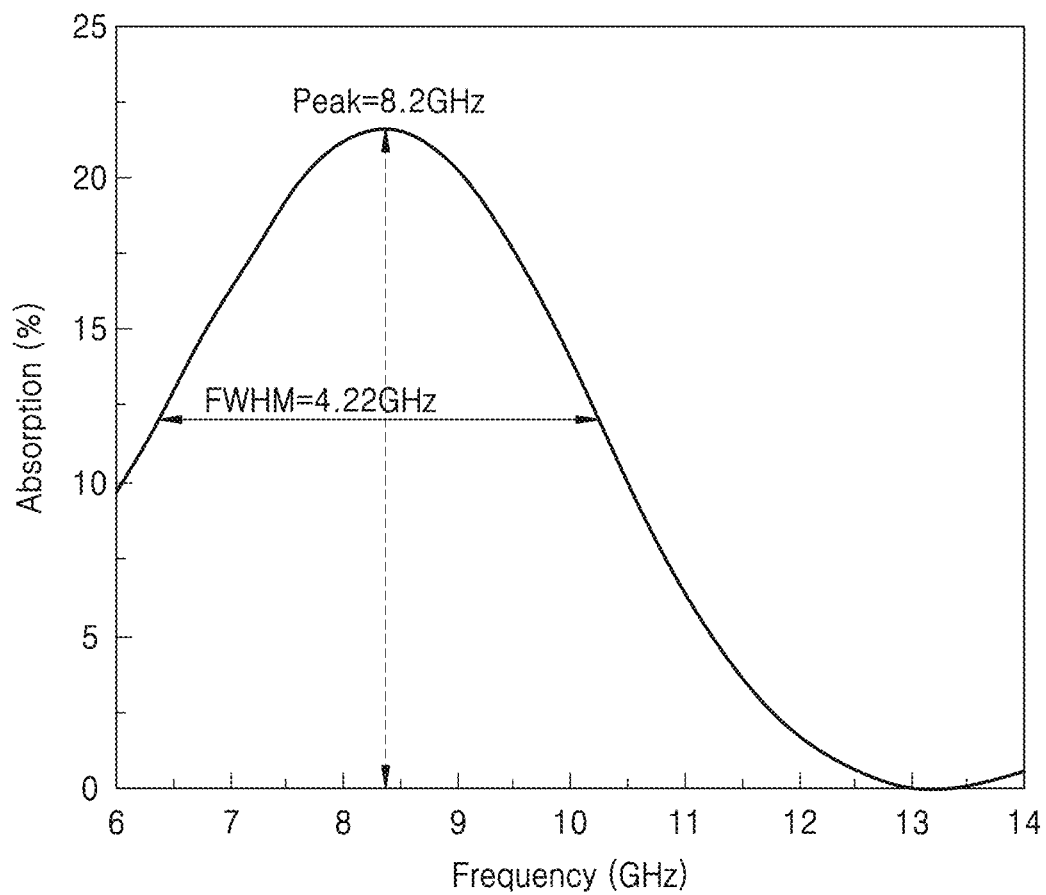
FIG. 2 is a graph illustrating the absorption of electromagnetic waves in H3N2 viruses with respect to the frequency of the electromagnetic waves.
Figure 3:
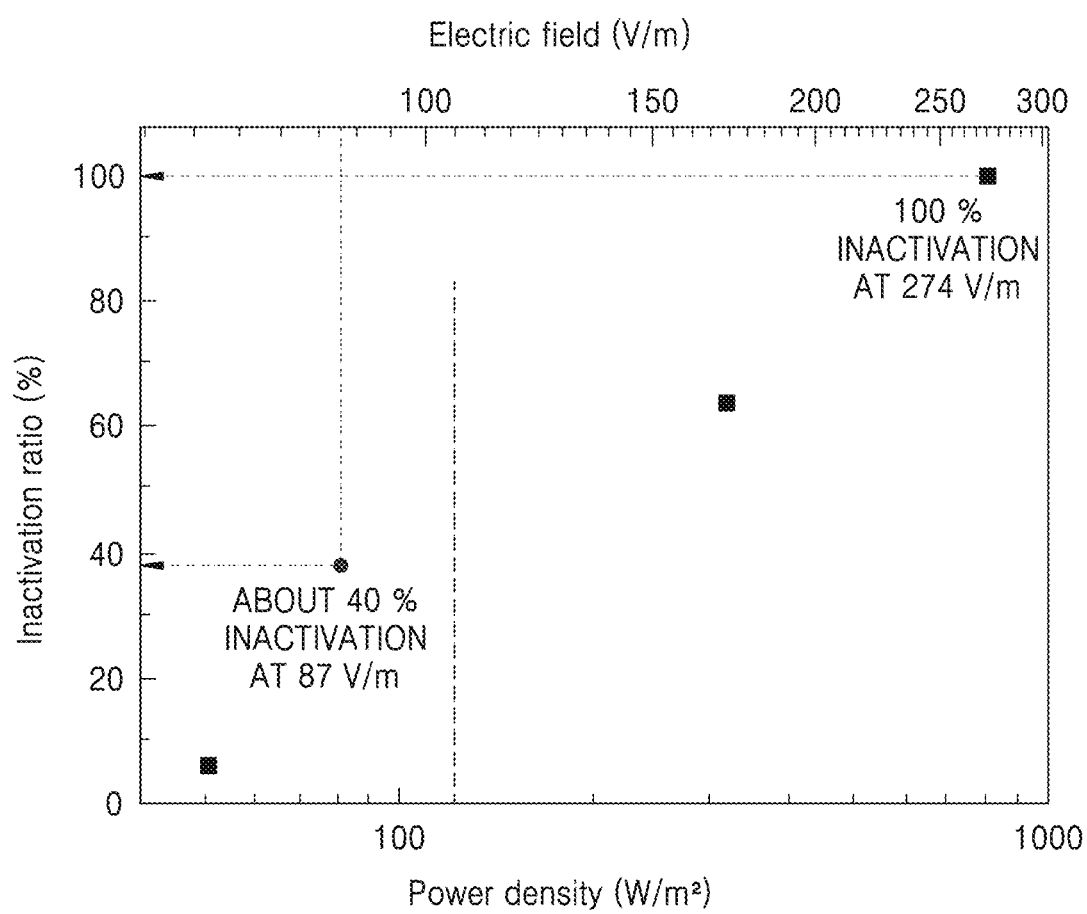
FIG. 3 is a graph illustrating the degree of inactivation of H3N2 viruses according to the intensity of electromagnetic waves.
Figure 5:
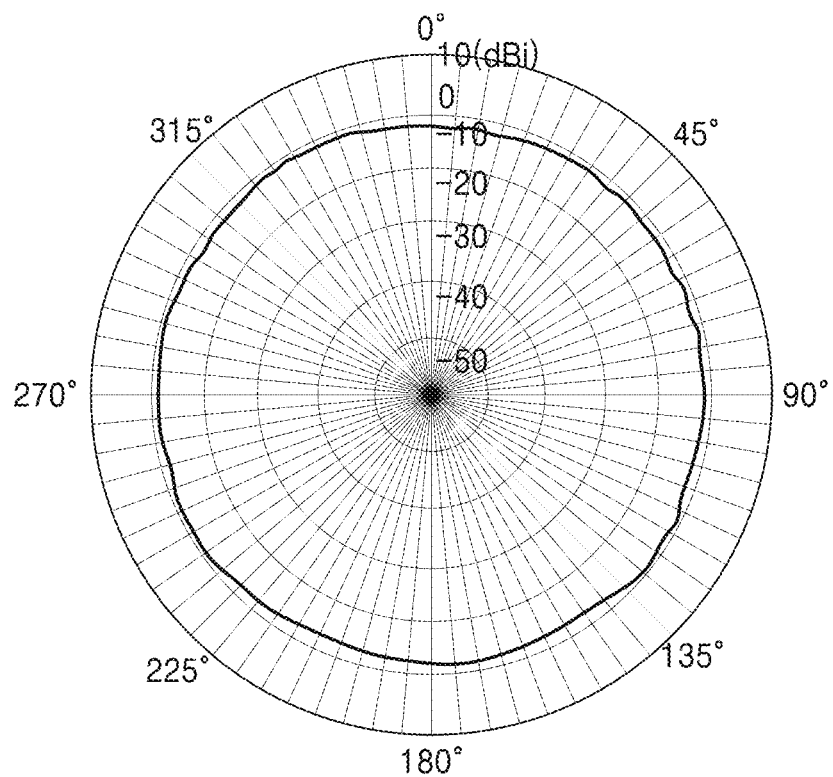
FIG. 5 is a view illustrating electromagnetic wave radiation characteristics of an antenna unit included in the object inactivating device shown in FIG. 1.

FIG. 1 is a schematic view illustrating an example structure of an object inactivating device 100 according to an embodiment. FIG. 2 is a graph illustrating the absorption of electromagnetic waves in H3N2 viruses with respect to the frequency of the electromagnetic waves. FIG. 3 is a graph illustrating the degree of inactivation of H3N2 viruses according to the intensity of electromagnetic waves. FIG. 4 is a table illustrating the strength of electromagnetic waves generated from various electronic devices. FIG. 5 is a view illustrating electromagnetic wave radiation characteristics of an antenna unit 20 included in the object inactivating device 100 shown in FIG. 1.

Referring to FIG. 1, the object inactivating device 100 may include: at least one electromagnetic wave generator 10 configured to generate an electromagnetic wave of which the frequency includes a resonant frequency of an object OBJ; and the antenna unit 20 electrically connected to the at least one electromagnetic wave generator 10 and configured to omni-directionally transmit the electromagnetic wave generated by the at least one electromagnetic wave generator 10.

For example, the object OBJ may include any one or any combination of any two or more of cells, germs, and viruses. In this case, the object OBJ may be inactivated by an electromagnetic wave radiated from the object inactivating device 100. For example, the object OBJ may be an H3N2 virus. H3N2 refers to a type of influenza viruses that cause influenza every year. However, the object OBJ is not limited to cells, germs, viruses, and the like, and examples of the object OBJ may include various objects that may be inactivated by electromagnetic waves radiated from the object inactivating device 100.

Cells, germs, viruses, and the like may have membranes made of proteins. In particular, viruses may have a capsid, which is a protein shell surrounding a genomic nucleic acid. The capsid is made up of a plurality of capsomeres regularly arranged in the outer shell of a virus. The capsid of a virus has a unique resonant frequency. When an electromagnetic wave corresponding to the resonant frequency of the capsid is applied to the capsid, the capsid may resonate, and as a result, the virus may be inactivated.

For example, as shown in FIG. 2, H3N2 viruses may exhibit the highest absorptance for 8.2 GHz electromagnetic waves. H3N2 viruses may have an absorptance of about 22% for 8.2 GHz electromagnetic waves. In other words, 8.2 GHz may be the resonant frequency of H3N2 viruses, and in this case, the full width at half maximum (FWHM) of the absorptance of H3N2 viruses may be about 4.22 GHz.

The capsids of H3N2 viruses may be damaged due to internal resonance occurring as the H3N2 viruses absorb 8.2 GHz electromagnetic waves corresponding to the resonant frequency of the capsids. Therefore, the H3N2 viruses may be inactivated as a result of internal resonance. For example, as shown in FIG. 3, when H3N2 viruses absorb electromagnetic waves having a frequency of 8.2 GHz and a strength of 87 V/m for about 15 minutes, about 40% of the H3N2 viruses may be inactivated. In addition, when H3N2 viruses absorb electromagnetic waves having a frequency of 8.2 GHz and a strength of 274 V/m for about 15 minutes, about 100% of the H3N2 viruses may be inactivated. However, electromagnetic waves with a strength of 274V/m may be harmful to the human body in which H3N2 viruses parasitize.

In addition, as shown in FIG. 4, electromagnetic waves generated from various electronic devices may have an intensity of 200 V/m or less. For example, the intensity of electromagnetic waves at a distance of 50 cm from a microwave oven may be about 25 V/m. The intensity of electromagnetic waves at a distance of 50 cm from a humidifier may be about 30 V/m. The intensity of electromagnetic waves at a distance of 30 cm from a washing machine may be about 70 V/m. The intensity of electromagnetic waves at a distance of 10 cm from a hair dryer may be about 105 V/m. The intensity of electromagnetic waves at a distance of 10 cm from a vacuum cleaner may be about 175 V/m.

The object inactivating device 100 may inactivate the object OBJ using an electromagnetic wave having an intensity of less than 200 V/m. For example, the object inactivating device 100 may selectively inactivate viruses or the like while minimizing the effect of electromagnetic waves on the human body by using an electromagnetic wave having an intensity of about 100 V/m or less, which is less than the average strength of electromagnetic waves generated from electronic devices.

The at least one electromagnetic wave generator 10 may generate an electromagnetic wave having a resonant frequency of the object OBJ to be inactivated. In addition, the at least one electromagnetic wave generator 10 may generate an electromagnetic wave in a frequency band of which the width is about 50% of the resonant frequency of the object OBJ.

Furthermore, the at least one electromagnetic wave generator 10 may generate an electromagnetic wave of which the frequency includes various resonant frequencies that the object OBJ may have. For example, the at least one electromagnetic wave generator 10 may generate an electromagnetic wave of which the frequency includes 8.2 GHz, which is a resonant frequency of H3N2 viruses. Alternatively, the at least one electromagnetic wave generator 10 may generate an electromagnetic wave of which the frequency includes 7.0 GHz, which is a resonant frequency of H1N1 viruses. In this way, the at least one electromagnetic wave generator 10 may generate an electromagnetic wave having a frequency within the range of about 5 GHz to about 10 GHz. Electromagnetic waves having a frequency within the range of about 5 GHz to about 10 GHz may correspond to the resonance frequencies of various types of viruses. However, embodiments are not limited thereto, and the at least one electromagnetic wave generator 10 may generate electromagnetic waves in various frequency ranges.

In addition, the at least one electromagnetic wave generator 10 may generate an electromagnetic wave having an intensity suitable for inactivating viruses or the like without damaging the human body. The at least one electromagnetic wave generator 10 may generate an electromagnetic wave having an intensity of less than about 200 V/m. For example, the at least one electromagnetic wave generator 10 may generate an electromagnetic wave having an intensity within the range of about 80 V/m to about 90 V/m.

The antenna unit 20 may transmit an electromagnetic wave generated by the at least one electromagnetic wave generator 10. In addition, the antenna unit 20 may be configured to uniformly transmit an electromagnetic wave in all directions. The antenna unit 20 may include an isotropic antenna device that uniformly transmit an electromagnetic wave in all directions as described above. For example, as shown in FIG. 5, the antenna unit 20 may transmit an electromagnetic wave which is close to 0 dBi in all directions. In other words, the antenna unit 20 may be configured to transmit an electromagnetic wave in all directions with uniform intensity in all directions.

The object inactivating device 100 may further include a substrate (not shown) having a first surface and a second surface which face each other. In this case, the at least one electromagnetic wave generator 10 may be provided on the first surface of the substrate, and the antenna unit 20 may be provided on the second surface of the substrate. The substrate may be of various types. An example structure of the object inactivating device 100 including the substrate will be described later with reference to FIG. 6.

Figure 6:
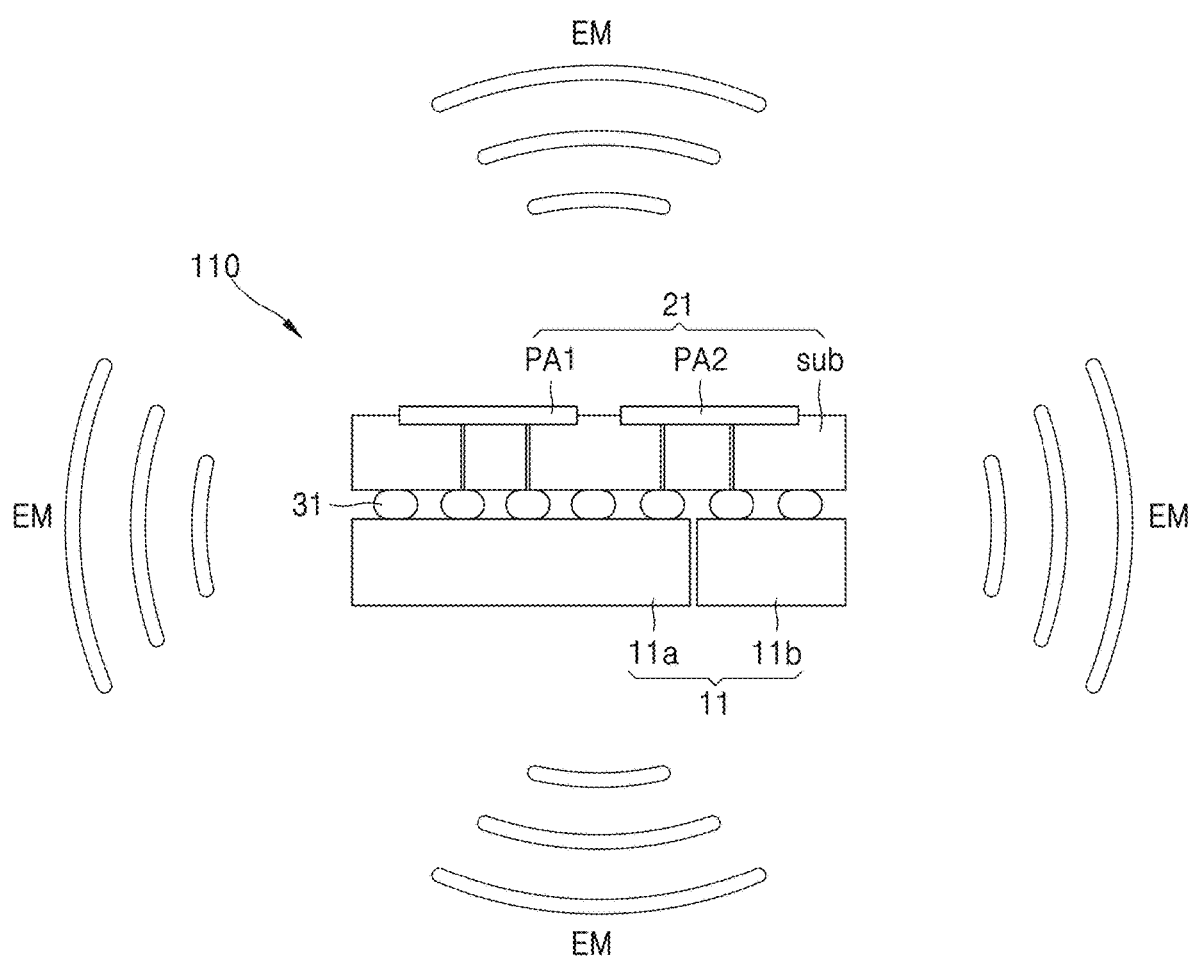
FIG. 6 is a side cross-sectional view schematically illustrating an example structure of an object inactivating device according to another embodiment.

FIG. 6 is a side cross-sectional view schematically illustrating an example structure of an object inactivating device 110 according to another embodiment.

Referring to FIG. 6, the object inactivating device 110 may include: at least one electromagnetic wave generator 11 configured to generate an electromagnetic wave having a resonant frequency of an object OBJ (refer to FIG. 1); and an antenna unit 21 electrically connected to the at least one electromagnetic wave generator 11 and configured to omni-directionally transmit the electromagnetic wave generated by the at least one electromagnetic wave generator 11.

The at least one electromagnetic wave generator 11 may generate an electromagnetic wave having a resonant frequency of the object OBJ to be inactivated. For example, the at least one electromagnetic wave generator 11 may generate an electromagnetic wave having a frequency within the range of about 5 GHz to about 10 GHz. In addition, for example, the at least one electromagnetic wave generator 11 may generate an electromagnetic wave having an intensity within the range of about 80 V/m to about 90 V/m.

The at least one electromagnetic wave generator 11 may include a semiconductor device configured to generate an electromagnetic wave. For example, the at least one electromagnetic wave generator 11 may include a radio frequency integrated circuit (RFIC) 11a. In addition, the at least one electromagnetic wave generator 11 may further include a crystal oscillator 11b configured to generate a frequency. An electromagnetic wave having a resonant frequency of the object OBJ may be generated by the RFIC 11a and the crystal oscillator 11b which are included in the at least one electromagnetic wave generator 11.

The antenna unit 21 may be configured such that an electromagnetic wave generated by the at least one electromagnetic wave generator 11 may be transmitted in all direction with uniform intensity in all directions. For example, the antenna unit 21 may include a low temperature co-fired ceramic (LTCC) substrate sub, and one or more patch antennas PA1 and PA2 provided on an upper portion of the LTCC substrate sub. In this case, the relative dielectric constant of the antenna unit 21 may be about 9 or more. Therefore, the antenna unit 21 is capable of transmitting an electromagnetic wave having a relatively low frequency, and the antenna unit 21 may have a compact structure, at the same time.

The at least one electromagnetic wave generator 11 may be provided under the LTCC substrate sub. For example, a plurality of via holes may be formed in the LTCC substrate sub, and the one or more patch antennas PA1 and PA2 may be electrically connected to the at least one electromagnetic wave generator 11 provided under the LTCC substrate sub through the via holes. The object inactivating device 110 may further include a ball grid array (BGA) 31. The at least one electromagnetic wave generator 11 and the antenna unit 21 may be electrically connected to each other through the BGA 31. For example, the BGA 31 may be provided under the via holes formed in the LTCC substrate sub to electrically connect the one or more patch antennas PA1 and PA2 and the at least one electromagnetic wave generator 11 to each other.

Figure 7:
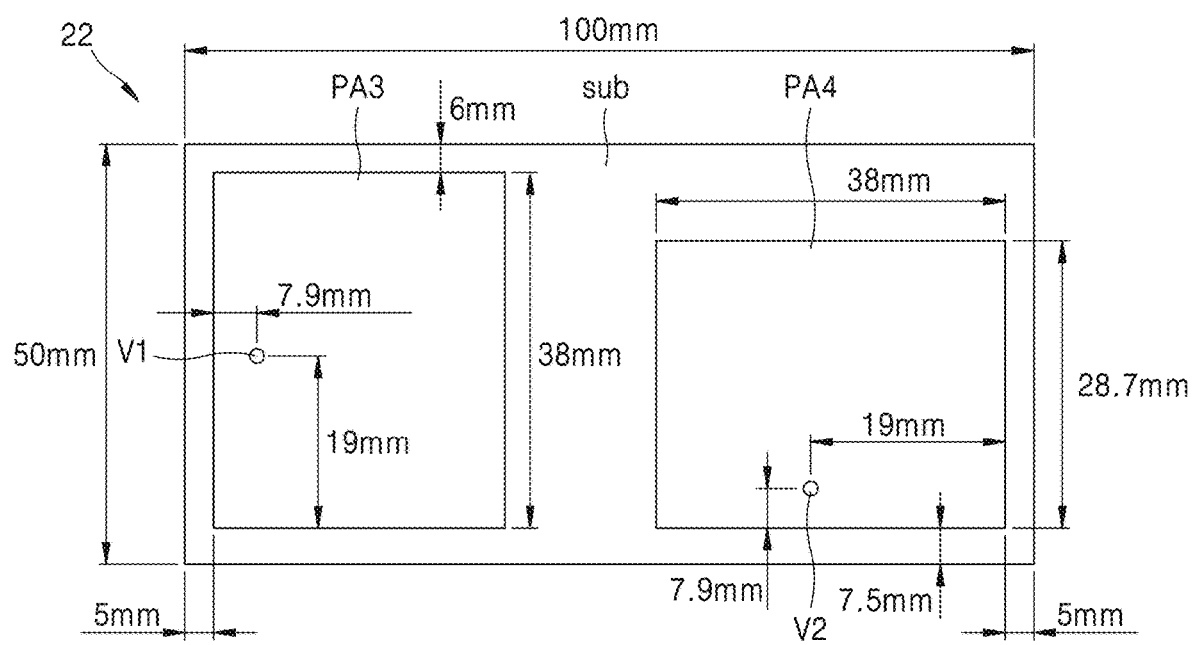
FIG. 7 is a schematic plan view illustrating an example structure of an antenna unit that may be included in the object inactivating device shown in FIG. 6.

FIG. 7 is a schematic plan view illustrating an example structure of an antenna unit 22 that may be included in the object inactivating device 110 shown in FIG. 6. The shape, dimensions, etc. of the antenna unit 22 shown in FIG. 7 are non-limiting examples.

Referring to FIG. 7, the antenna unit 22 may include an LTCC substrate sub and one or more patch antennas PA3 and PA4 provided on the LTCC substrate sub. The one or more patch antennas PA3 and PA4 may include a first patch antenna PA3 and a second patch antenna PA4 which have rectangular flat surfaces. In this case, the first patch antenna PA3 may have a vertical length of about 38 mm and a horizontal length of about 28.7 mm. In addition, the second patch antenna PA4 may have a horizontal length of about 38 mm and a vertical length of about 28.7 mm. The first patch antenna PA3 and the second patch antenna PA4 may be apart from each other on the LTCC substrate sub having a horizontal length of about 100 mm and a vertical length of about 50 mm. For example, the separation distance between the first patch antenna PA3 and the second patch antenna PA4 may be about 23.3 mm. The first patch antenna PA3 and the second patch antenna PA4 may respectively include via holes V1 and V2 each about 7.9 mm away from the long side and about 19 mm away from the short side.

Figure 8:
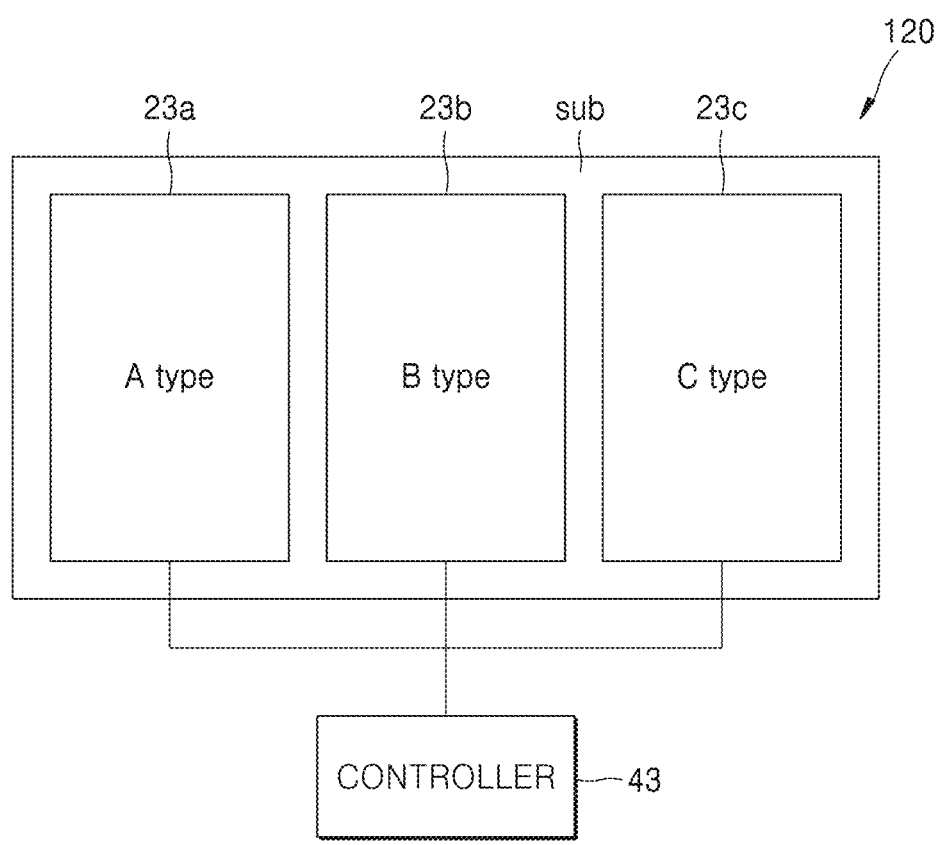
FIG. 8 is a schematic view illustrating an example structure of an object inactivating device according to another embodiment.

FIG. 8 is a schematic view illustrating an example structure of an object inactivating device 120 according to another embodiment. The basic configuration of the object inactivating device 120 is similar to that of the object inactivating device 110 shown in FIG. 6. In the description given below with reference to FIG. 8, structural characteristics of the object inactivating device 120 which are different from those of the object inactivating device 110 shown in FIG. 6 will be described, and the same characteristics as those of the object inactivating device 110 shown in FIG. 6 will not be described.

Referring to FIG. 8, the object inactivating device 120 may include: a first electromagnetic wave generator (not shown) configured to generate a first electromagnetic wave having a first frequency; and a second electromagnetic wave generator (not shown) configured to generate a second electromagnetic wave having a second frequency different from the first frequency. In addition, the object inactivating device 120 may further include a third electromagnetic wave generator (not shown) configured to generate a third electromagnetic wave having a third frequency different from the first frequency and the second frequency.

In addition, the object inactivating device 120 may include a first antenna unit 23a, a second antenna unit 23b, and a third antenna unit 23c that are electrically connected to the first electromagnetic wave generator, the second electromagnetic wave generator, and the third electromagnetic wave generator, respectively. The first antenna unit 23a may transmit the first electromagnetic wave having the first frequency and generated by the first electromagnetic wave generator. In addition, the second antenna unit 23b may transmit the second electromagnetic wave having the second frequency and generated by the second electromagnetic wave generator. Furthermore, the third antenna unit 23c may transmit the third electromagnetic wave having the third frequency and generated by the third electromagnetic wave generator. In this case, the first electromagnetic wave generator, the second electromagnetic wave generator, and the third electromagnetic wave generator may be sequentially classified into A, B, and C types. The first, second, and third frequencies of electromagnetic waves generated by the first, second, and third electromagnetic wave generators may respectively be resonant frequencies of different types of cells, germs, viruses, etc.

The object inactivating device 120 may further include a controller 43 configured to selectively operate the first electromagnetic wave generator, the second electromagnetic wave generator, and the third electromagnetic wave generator. For example, when it is intended to inactivate a first object having a resonant frequency corresponding to the first frequency, the controller 43 may operate the first electromagnetic wave generator to generate the first frequency and may stop the second electromagnetic wave generator and the third electromagnetic wave generator. In addition, when it is intended to inactivate a second object having a resonant frequency corresponding to the second frequency, the controller 43 may operate the second electromagnetic wave generator to generate the second frequency and may stop the first electromagnetic wave generator and the third electromagnetic wave generator. Furthermore, when it is intended to inactivate a third object having a resonant frequency corresponding to the third frequency, the controller 43 may operate the third electromagnetic wave generator to generate the third frequency and may stop the first electromagnetic wave generator and the second electromagnetic wave generator.

Various objects (refer to the object OBJ in FIG. 1) having different resonant frequencies may be selectively inactivated as needed by using the object inactivating device 120 configured to radiate electromagnetic waves having various frequencies as described above.

Figure 9:
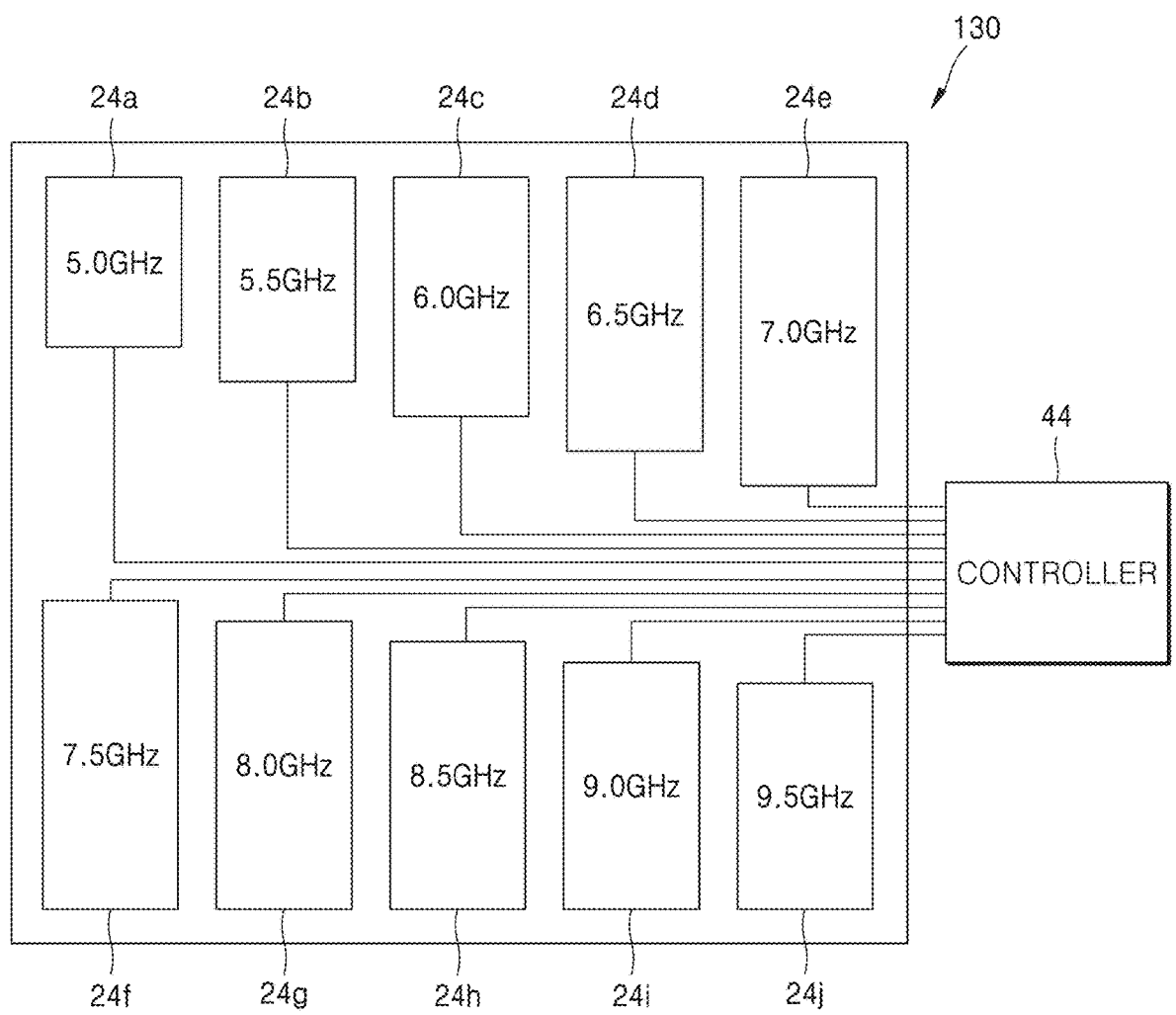
FIG. 9 is a schematic view illustrating an example structure of an object inactivating device according to another embodiment.

FIG. 9 is a schematic view illustrating an example structure of an object inactivating device 130 according to another embodiment. The basic configuration of the object inactivating device 130 is similar to that of the object inactivating device 110 shown in FIG. 6. In the description given below with reference to FIG. 8, structural characteristics of the object inactivating device 130 which are different from those of the object inactivating device 110 shown in FIG. 6 will be described, and the same characteristics as those of the object inactivating device 110 shown in FIG. 6 will not be described.

Referring to FIG. 9, the object inactivating device 130 may include a plurality of electromagnetic wave generators (not shown) which respectively generate a plurality of electromagnetic waves having a plurality of different frequencies. The frequencies of the plurality of electromagnetic waves generated by the plurality of electromagnetic wave generators may be different from each other with step-by-step increments therebetween. For example, among the plurality of electromagnetic wave generators, a first electromagnetic wave generator (not shown) may generate an electromagnetic wave having a frequency of about 5 GHz, a second electromagnetic wave generator (not shown) may generate an electromagnetic wave having a frequency of about 5.5 GHz, and a third electromagnetic wave generator (not shown) may generate an electromagnetic wave having a frequency of about 6.0 GHz. As described above, the frequencies of electromagnetic waves generated by the plurality of electromagnetic wave generators be different from each other with a step-by-step increment of about 0.5 GHz. However, embodiments are not limited thereto, and the frequency difference between electromagnetic waves generated by the plurality of electromagnetic wave generators may be less than or greater than about 0.5 GHz. In addition, the frequency difference between electromagnetic waves generated by the electromagnetic wave generators may not be constant.

Furthermore, the object inactivating device 130 may include a plurality of antenna units 24a to 24j. The electromagnetic wave generators may be electrically connected to the antenna units 24a to 24j, respectively. Among the antenna units 24a to 24j, a first antenna unit 24a may transmit a first electromagnetic wave having a frequency of about 5 GHz and generated by the first electromagnetic wave generator. In addition, among the antenna units 24a to 24j, a second antenna unit 24b may transmit a second electromagnetic wave having a frequency of about 5.5 GHz and generated by the second electromagnetic wave generator. Furthermore, among the antenna units 24a to 24j, a third antenna unit 24c may transmit a third electromagnetic wave having a frequency of about 6.0 GHz and generated by the third electromagnetic wave generator.

The object inactivating device 130 may further include a controller 44 configured to selectively operate the electromagnetic wave generators. The controller 44 may sequentially operate the electromagnetic wave generators for a predetermined time period. For example, while the first electromagnetic wave generator generates a first electromagnetic wave having the first frequency for a first time period, the controller 44 may stop the other electromagnetic wave generators. In addition, while the second electromagnetic wave generator generates a second electromagnetic wave having the second frequency for a second time period, the controller 44 may stop the other electromagnetic wave generators.

Therefore, a plurality of electromagnetic waves having different frequencies may be sequentially radiated from the object inactivating device 130, and an object OBJ (refer to FIG. 1) located adjacent to the object inactivating device 130 may be inactivated by an electromagnetic wave having a resonant frequency of the object OBJ among the plurality of electromagnetic waves.

When the electromagnetic wave generators configured to generate a plurality of electromagnetic waves having different frequencies as described above, even an object OBJ of which the resonant frequency is not known may be effectively inactivated by sequentially operating the electromagnetic wave generators.

Figure 10:
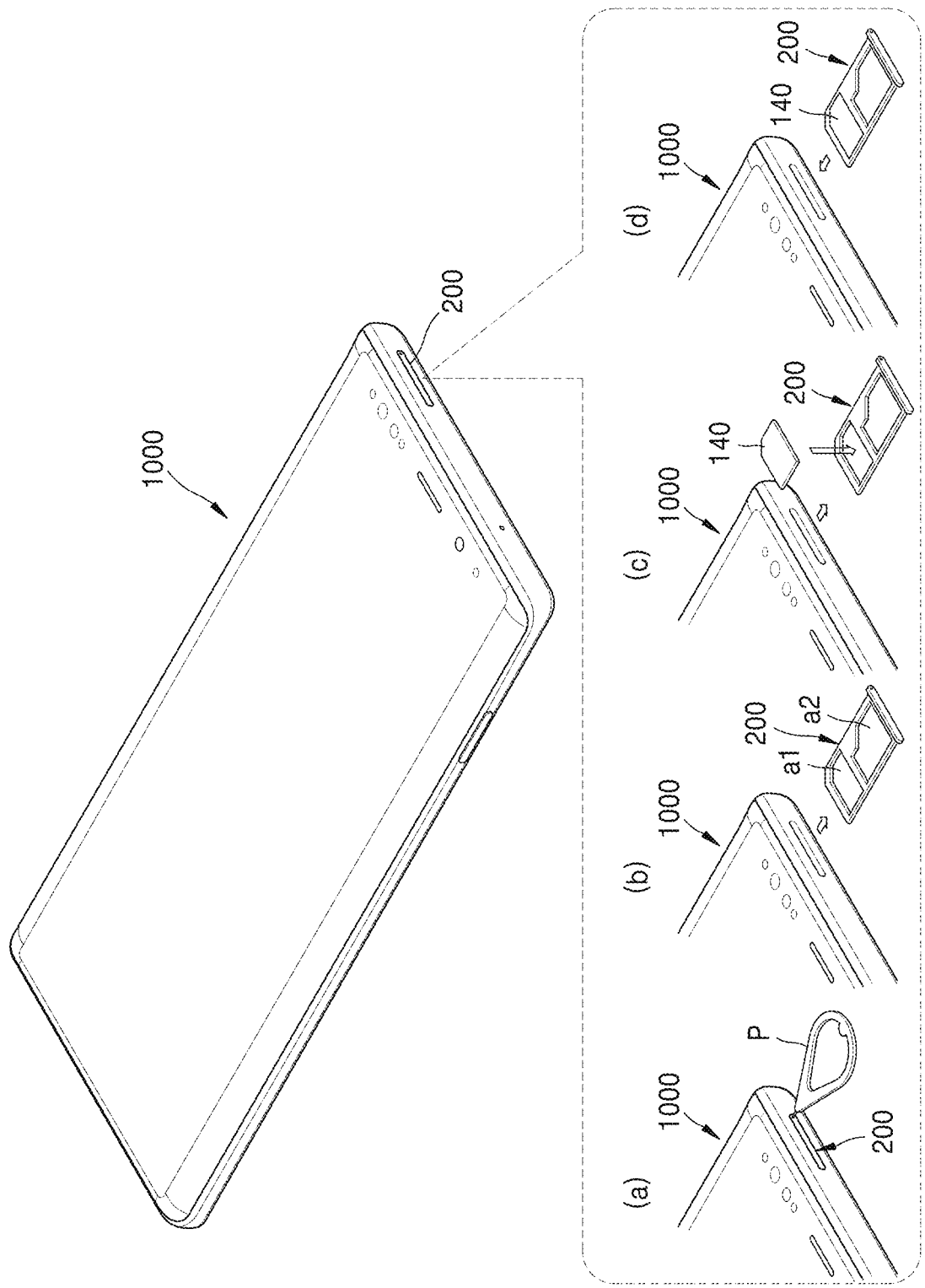
FIG. 10 is a schematic view illustrating an example structure of an electronic device including an object inactivating device according to an embodiment.

FIG. 10 is a schematic view illustrating an example structure of an electronic device 1000 including an object inactivating device 140 according to an embodiment. The electronic device 1000 may be implemented as at least one selected from the group consisting of a smartphone, a tablet PC, and a wearable device. The following description will be given for the case in which the electronic device 1000 is a smartphone. However, the following description given with reference to FIG. 10 may be applied to other cases in which the electronic device 1000 is implemented as various devices other than a smart phone.

Referring to FIG. 10, the electronic device 1000 may include the object inactivating device 140 and a mount 200 on which the object inactivating device 140 is mounted.

The object inactivating device 140 may include any one of the object inactivating devices 100, 110, 120, and 130 described with reference to FIGS. 1 to 9.

The mount 200 may include a structure in which the object inactivating device 140 may be mounted. The mount 200 may be, for example, a USIM chip tray. In this case, the mount 200 may have a tray shape insertable into the electronic device 1000 and may have a mounting region a1 in which the object inactivating device 140 is mountable. In addition, the mount 200 may further include a core region a2 in which the USIM chip is mountable. As shown in FIG. 10, the mount 200 inserted into the electronic device 1000 may be separated from the electronic device 1000 by using a pin P. The object inactivating device 140 may be mounted in the mounting region a1 of the mount 200 separated from the electronic device 1000. Then, the mount 200 on which the object inactivating device 140 is mounted may be inserted into the electronic device 1000 again. Various types of objects in the electronic device 1000 may be inactivated using the object inactivating device 140 inserted into the electronic device 1000 as described above.

Although FIG. 10 illustrates the case in which the electronic device 1000 is a smartphone, embodiments are not limited thereto, and examples of the electronic device 1000 may include various types of devices such as a desktop, a laptop, and a home appliance. In this case, the mount 200 may be provided in various forms to allow the object inactivating device 140 to be installed in the electronic device 1000.

Figure 11:
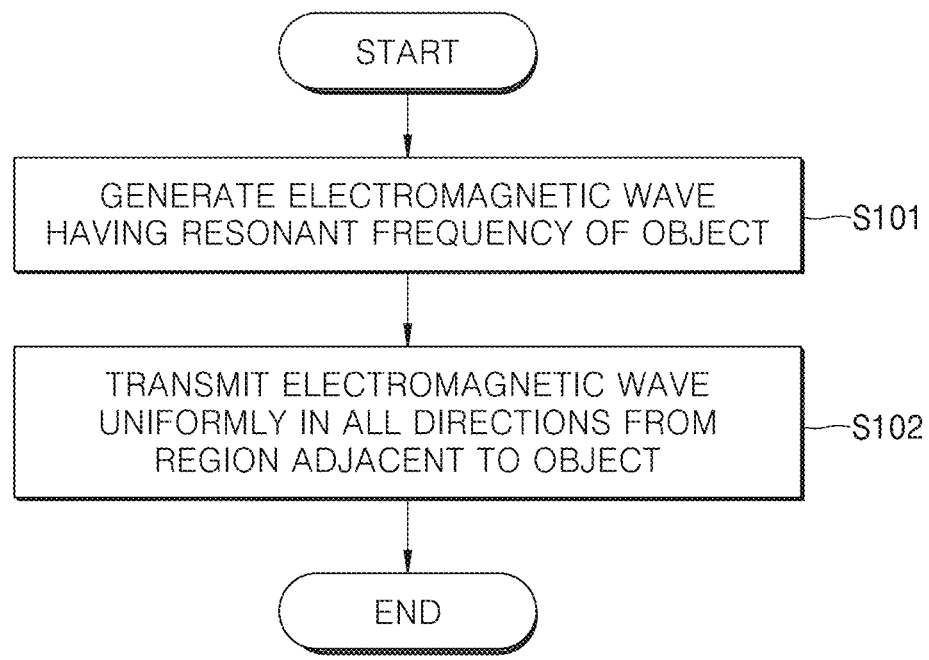
FIG. 11 is a flowchart illustrating a method of inactivating an object according to an embodiment.

FIG. 11 is a flowchart illustrating a method of inactivating an object according to an embodiment.

Referring to FIG. 11, the method of inactivating an object according to an embodiment may include an operation S101 of generating an electromagnetic wave having a resonant frequency of an object, and an operation S102 of uniformly transmitting the electromagnetic wave in all directions from a region adjacent to the object.

In the operation S101 of generating an electromagnetic wave, electromagnetic waves may be generated using various types of electromagnetic wave generators. For example, an electromagnetic wave may be generated using a device including an RFIC and a crystal oscillator. In addition, in the operation S101 of generating an electromagnetic wave, an electromagnetic wave having an intensity within the range of about 80 V/m to about 90 V/m and a frequency within the range of about 5 GHz to about 10 GHz may be generated.

In the operation S102 of transmitting the electromagnetic wave, the generated electromagnetic wave may be uniformly transmitted in all directions, and thus even when the object is apart in an arbitrary direction from the point at which the electromagnetic wave is generated, the object may be equally inactivated.

Figure 12:
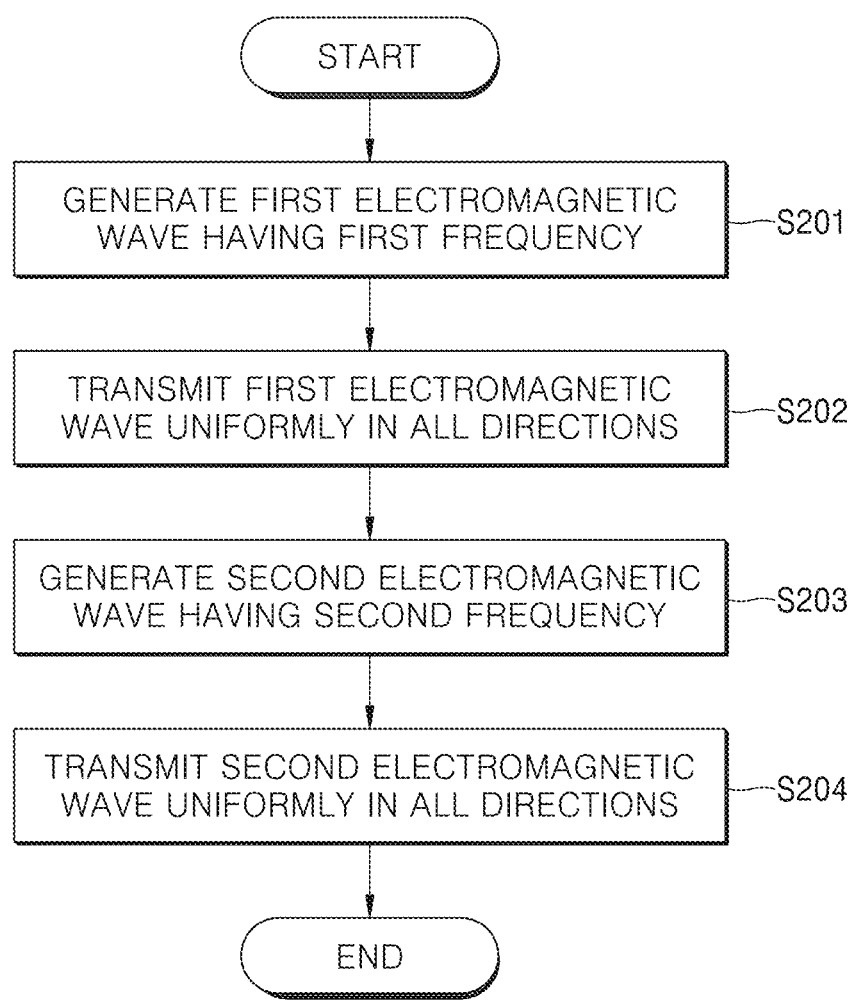
FIG. 12 is a flowchart illustrating a method of inactivating an object according to another embodiment.

FIG. 12 is a flowchart illustrating a method of inactivating an object according to another embodiment.

Referring to FIG. 12, the method of inactivating an object according to another embodiment may include: an operation S201 of generating a first electromagnetic wave having a first frequency; an operation S202 of uniformly transmitting the first electromagnetic wave in all directions; an operation S203 of generating a second electromagnetic wave having a second frequency different from the first frequency; and an operation S204 of uniformly transmitting the second electromagnetic wave in all directions. In this case, after the first electromagnetic wave having the first frequency is generated and transmitted for a first time period, the second electromagnetic wave having the second frequency may be generated and transmitted for a second time period.

The first frequency and the second frequency may correspond to different resonance frequencies of different objects. Different objects may be selectively inactivated by sequentially radiating electromagnetic waves having different frequencies for given time periods as described above.

As described above, embodiments of the present disclosure may provide devices for selectively inactivating an object in a non-contact manner, electronic devices including the devices, and methods of inactivating an object.

According to the various embodiments of the present disclosure, objects such as cells, germs, and viruses may be selectively inactivated using electromagnetic waves having resonant frequencies of the objects.

The object inactivating device 100, 120, 130 in FIGS. 1-12 that perform the operations described in this application are implemented by hardware components configured to perform the operations described in this application that are performed by the hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 1-12 that perform the operations described in this application are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control computing hardware, for example, one or more processors or computers, to implement the hardware components and perform the methods as described above may be written as computer programs, code segments, instructions or any combination thereof, for individually or collectively instructing or configuring the one or more processors or computers to operate as a machine or special-purpose computer to perform the operations that are performed by the hardware components and the methods as described above. In one example, the instructions or software include machine code that is directly executed by the one or more processors or computers, such as machine code produced by a compiler. In another example, the instructions or software includes higher-level code that is executed by the one or more processors or computer using an interpreter. The instructions or software may be written using any programming language based on the block diagrams and the flow charts illustrated in the drawings and the corresponding descriptions in the specification, which disclose algorithms for performing the operations that are performed by the hardware components and the methods as described above.

The instructions or software to control computing hardware, for example, one or more processors or computers, to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any other device that is configured to store the instructions or software and any associated data, data files, and data structures in a non-transitory manner and provide the instructions or software and any associated data, data files, and data structures to one or more processors or computers so that the one or more processors or computers can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A device for inactivating an object, the device comprising:
    an electromagnetic wave circuitry that generates an electromagnetic wave with a first resonant frequency, and a frequency band with a width of about 50% of the first resonant frequency, the frequency band is within a range of about 5 GHz to 10 GHz; and
    an antenna electrically connected to the electromagnetic wave circuitry and omni-directionally transmitting the electromagnetic wave to inactivate the object.

2. The device of claim 1, wherein the object comprises any one or any combination of any two or more of cells, germs, and viruses.

3. The device of claim 1, wherein the electromagnetic wave circuitry generates the electromagnetic wave with an intensity of less than about 200 V/m.

4. The device of claim 1, wherein the antenna uniformly transmit the electromagnetic wave in all directions.

5. The device of claim 1, wherein the electromagnetic wave circuitry comprises a radio frequency integrated circuit (RFIC).

6. The device of claim 5, wherein the electromagnetic wave circuitry further comprises a crystal oscillator.

7. The device of claim 1, wherein the antenna comprises a low temperature co-fired ceramic (LTCC) substrate and a patch antenna provided on an upper portion of the LTCC substrate.

8. The device of claim 1, further comprising a substrate comprising a first surface and a second surface facing each other,
    wherein the electromagnetic wave circuitry is provided on the first surface of the substrate, and the antenna is provided on the second surface of the substrate.

9. The device of claim 1, wherein the electromagnetic wave circuitry comprises:
    a first electromagnetic wave circuitry configured to generate a first electromagnetic wave having the first resonant frequency; and
    a second electromagnetic wave circuitry configured to generate a second electromagnetic wave having a second resonant frequency different from the first resonant frequency.

10. The device of claim 9, wherein the electromagnetic wave circuitry further comprises a third electromagnetic wave circuitry configured to generate a third electromagnetic wave having a third resonant frequency different from the first resonant frequency and the second resonant frequency,
    wherein the first resonant frequency, the second resonant frequency, and the third resonant frequency are different from each other by a constant increment size.

11. The device of claim 9, further comprising a controller configured to selectively operate the first electromagnetic wave circuitry and the second electromagnetic wave circuitry.

12. The device of claim 9, wherein the antenna comprises:
a first antenna electrically connected to the first electromagnetic wave circuitry; and
a second antenna electrically connected to the second electromagnetic wave circuitry.

13. The device of claim 1, wherein the device is an electronic device; and
wherein the device comprises a mount on which the electronic device is mounted.

14. The device of claim 13, wherein the electronic device comprises at least one selected from the group consisting of a smartphone, a tablet PC, and a wearable device.

15. A method comprising:
generating an electromagnetic wave with a first resonant frequency, and a frequency band with a width of about 50% of the first resonant frequency, the frequency band is within a range of about 5 GHz to 10 GHz; and
transmitting the electromagnetic wave uniformly in all directions from a position adjacent to the object.

16. The method of claim 15, wherein in the generating of the electromagnetic wave, the electromagnetic wave has an intensity lower than about 200 V/min.

17. The method of claim 15,
wherein the electromagnetic wave is a first electromagnetic wave, and after generating and transmitting the first electromagnetic wave,
the method further comprises:
generating a second electromagnetic wave having a second resonant frequency different from the first resonant frequency; and
transmitting the second electromagnetic wave uniformly in all directions from a position adjacent to the object.

18. The method of claim 1, wherein the antenna omnidirectionally transmits the electromagnetic wave with uniform intensity in all directions.

* * * * *